(12) United States Patent
Khan et al.

(10) Patent No.: US 12,080,433 B2
(45) Date of Patent: Sep. 3, 2024

(54) HEALTHCARE APPLICATION INSIGHT COMPILATION SENSITIVITY

(71) Applicant: INTERNATIONAL BUSINESS MACHINES CORPORATION, Armonk, NY (US)

(72) Inventors: Shakil Manzoor Khan, Highland Mills, NY (US); Paul R. Bastide, Ashland, MA (US); Senthil Bakthavachalam, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 298 days.

(21) Appl. No.: 17/248,844

(22) Filed: Feb. 10, 2021

(65) Prior Publication Data
US 2022/0254505 A1 Aug. 11, 2022

(51) Int. Cl.
| | |
|---|---|
| *G16H 50/70* | (2018.01) |
| *G06F 16/23* | (2019.01) |
| *G16H 10/60* | (2018.01) |
| *G16H 40/20* | (2018.01) |
| *G16H 70/20* | (2018.01) |

(52) U.S. Cl.
CPC ......... *G16H 50/70* (2018.01); *G06F 16/2379* (2019.01); *G16H 10/60* (2018.01); *G16H 40/20* (2018.01); *G16H 70/20* (2018.01)

(58) Field of Classification Search
CPC ........ G16H 50/70; G16H 40/20; G16H 10/60; G16H 70/20; G06F 16/2379; G06F 16/23
See application file for complete search history.

(56) References Cited

U.S. PATENT DOCUMENTS

| | | | | |
|---|---|---|---|---|
| 5,311,516 A | * | 5/1994 | Kuznicki | H04L 25/062 |
| | | | | 340/7.45 |
| 6,466,936 B1 | | 10/2002 | Mikael | |
| 6,539,026 B1 | * | 3/2003 | Waclawsky | H04L 47/805 |
| | | | | 370/428 |
| 7,292,956 B1 | | 11/2007 | Guday | |
| 7,779,031 B2 | * | 8/2010 | Grosset | G06F 16/283 |
| | | | | 715/255 |

(Continued)

FOREIGN PATENT DOCUMENTS

| | | | | |
|---|---|---|---|---|
| CN | 104184819 A | * | 12/2014 | |
| CN | 107066877 A | * | 8/2017 | ......... G06F 16/2358 |
| KR | 101946937 B1 | | 5/2018 | |

OTHER PUBLICATIONS

Mell, et al., "The NIST Definition of Cloud Computing", Recommendations of the National Institute of Standards and Technology, NIST Special Publication 800-145, Sep. 2011, 7 pages.

*Primary Examiner* — Kenneth Bartley
(74) *Attorney, Agent, or Firm* — Anthony R. Curro

(57) ABSTRACT

Dynamically moderating healthcare application data. Receive an incoming data load request comprising a plurality of referential data elements and assess a downstream query impact of the plurality of referential data elements. Determine, based on the assessing, a sensitivity level of the plurality of referential data elements, and alter, based on the sensitivity level, compilation of insights generated using the plurality of referential data elements and compilation of a plurality of referenced data elements.

18 Claims, 7 Drawing Sheets

(56) References Cited

U.S. PATENT DOCUMENTS

| | | | |
|---|---|---|---|
| 8,898,126 B1* | 11/2014 | Dai | G06F 16/2308 707/703 |
| 10,523,532 B1* | 12/2019 | Summers | H04L 41/40 |
| 10,776,368 B1* | 9/2020 | Caragea | G06F 16/2462 |
| 11,055,352 B1* | 7/2021 | Beitchman | G06F 16/90335 |
| 11,416,247 B1* | 8/2022 | Bastide | G06F 8/71 |
| 2004/0052304 A1* | 3/2004 | Reial | H04B 1/7113 375/E1.032 |
| 2005/0240354 A1* | 10/2005 | Mamou | G06Q 10/10 702/19 |
| 2006/0085592 A1* | 4/2006 | Ganguly | G06F 16/2456 711/114 |
| 2006/0111933 A1* | 5/2006 | Wheeler | G16Z 99/00 705/2 |
| 2007/0297327 A1* | 12/2007 | Strom | H04L 67/61 370/230 |
| 2008/0201293 A1* | 8/2008 | Grosset | G06F 16/283 |
| 2008/0239951 A1* | 10/2008 | Strom | H04L 67/62 370/230 |
| 2011/0161940 A1* | 6/2011 | Brunswig | G06F 8/40 717/139 |
| 2011/0258179 A1* | 10/2011 | Weissman | G06F 16/24537 707/713 |
| 2013/0254193 A1* | 9/2013 | Heidasch | G06F 16/9024 707/736 |
| 2013/0326048 A1* | 12/2013 | Heidasch | G06N 5/02 709/224 |
| 2013/0332194 A1 | 12/2013 | D'Auria | |
| 2014/0052713 A1* | 2/2014 | Schauer | G06F 16/244 707/E17.082 |
| 2014/0280042 A1* | 9/2014 | Lock | G06F 16/248 707/722 |
| 2015/0081908 A1* | 3/2015 | Tan | H04L 41/5025 709/226 |
| 2015/0113537 A1* | 4/2015 | Bourbonnais | G06F 11/16 718/103 |
| 2015/0154192 A1* | 6/2015 | Lysne | G06N 5/00 707/758 |
| 2015/0236945 A1* | 8/2015 | Michael | H04L 47/17 370/238 |
| 2016/0034553 A1* | 2/2016 | Tong | G06F 16/248 707/754 |
| 2017/0220633 A1* | 8/2017 | Porath | G06F 16/248 |
| 2018/0075012 A1* | 3/2018 | Allen | G16H 10/60 |
| 2018/0096103 A1* | 4/2018 | Allen | G16H 10/60 |
| 2018/0101598 A1* | 4/2018 | Allen | G06F 40/268 |
| 2018/0114595 A1* | 4/2018 | Stern | G16H 80/00 |
| 2018/0157796 A1* | 6/2018 | Jain | G06F 40/30 |
| 2018/0157797 A1 | 6/2018 | Perry | |
| 2019/0156947 A1 | 5/2019 | Nakamura | |
| 2020/0026786 A1* | 1/2020 | Cadarette | G06F 16/2365 |
| 2020/0074104 A1* | 3/2020 | Sommerville | G06F 21/6227 |
| 2020/0125568 A1* | 4/2020 | Idicula | G06N 20/20 |
| 2020/0160986 A1* | 5/2020 | Vegas Santiago | G16H 40/20 |
| 2020/0168345 A1 | 5/2020 | Bastide | |
| 2020/0296026 A1* | 9/2020 | Michael | H04L 43/08 |
| 2020/0356873 A1* | 11/2020 | Nawrocke | G06F 11/3409 |
| 2021/0004715 A1* | 1/2021 | Neumann | G16H 30/20 |
| 2021/0049548 A1* | 2/2021 | Grisz | G06Q 10/0831 |
| 2021/0248152 A1* | 8/2021 | Bastide | G06F 40/279 |
| 2021/0295822 A1* | 9/2021 | Tomkins | G06F 16/90332 |
| 2021/0313032 A1* | 10/2021 | Fotsch | G06F 16/2471 |
| 2022/0019586 A1* | 1/2022 | Wang | G06F 16/24542 |
| 2022/0138826 A1* | 5/2022 | Wang | G06F 16/9538 705/26.63 |

\* cited by examiner

HEALTHCARE APPLICATION INSIGHT COMPILATION SENSITIVITY

BACKGROUND

The present invention relates generally to data management and processing in a distributed computing environment, and more particularly to dynamically moderating healthcare application data, and to dynamically moderating healthcare application insight compilation velocity.

Healthcare systems generally refer to computing systems or computing environments adapted for use in the healthcare industry, for healthcare-related purposes, or to perform healthcare-related tasks. For example, a healthcare system may be configured to store and process electronic health records (EHR) of patients, and to execute workflows that use EHRs. In one implementation, the healthcare system may be a distributed computing system, which also may be referred to as a platform or a cloud platform. These terms will be used interchangeably as needed based on the specific context of embodiments of the claimed invention.

SUMMARY

Embodiments of the present invention provide methods, systems, and computer program products for dynamically moderating healthcare application data. An embodiment receives an incoming data load request comprising a plurality of referential data elements and assesses a downstream query impact of the plurality of referential data elements. The embodiment determines, based on the assessing, a sensitivity level of the plurality of referential data elements, and alters, based on the sensitivity level, compilation of insights generated using the plurality of referential data elements and compilation of a plurality of referenced data elements.

BRIEF DESCRIPTION OF THE DRAWINGS

The novel features believed to be characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

Figure 5:
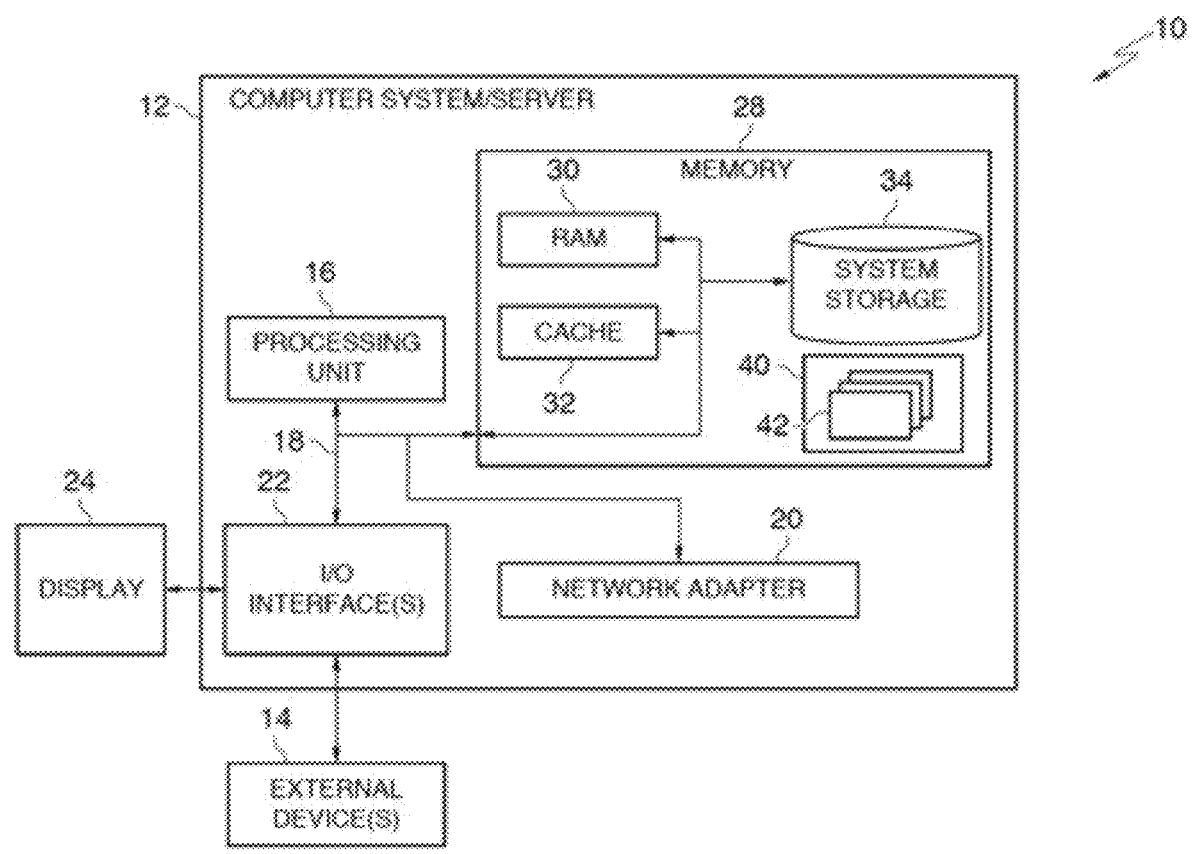
FIG. 5 is a functional block diagram 10 of a computing device or cloud computing node, according to an embodiment of the invention.
Figure 6:
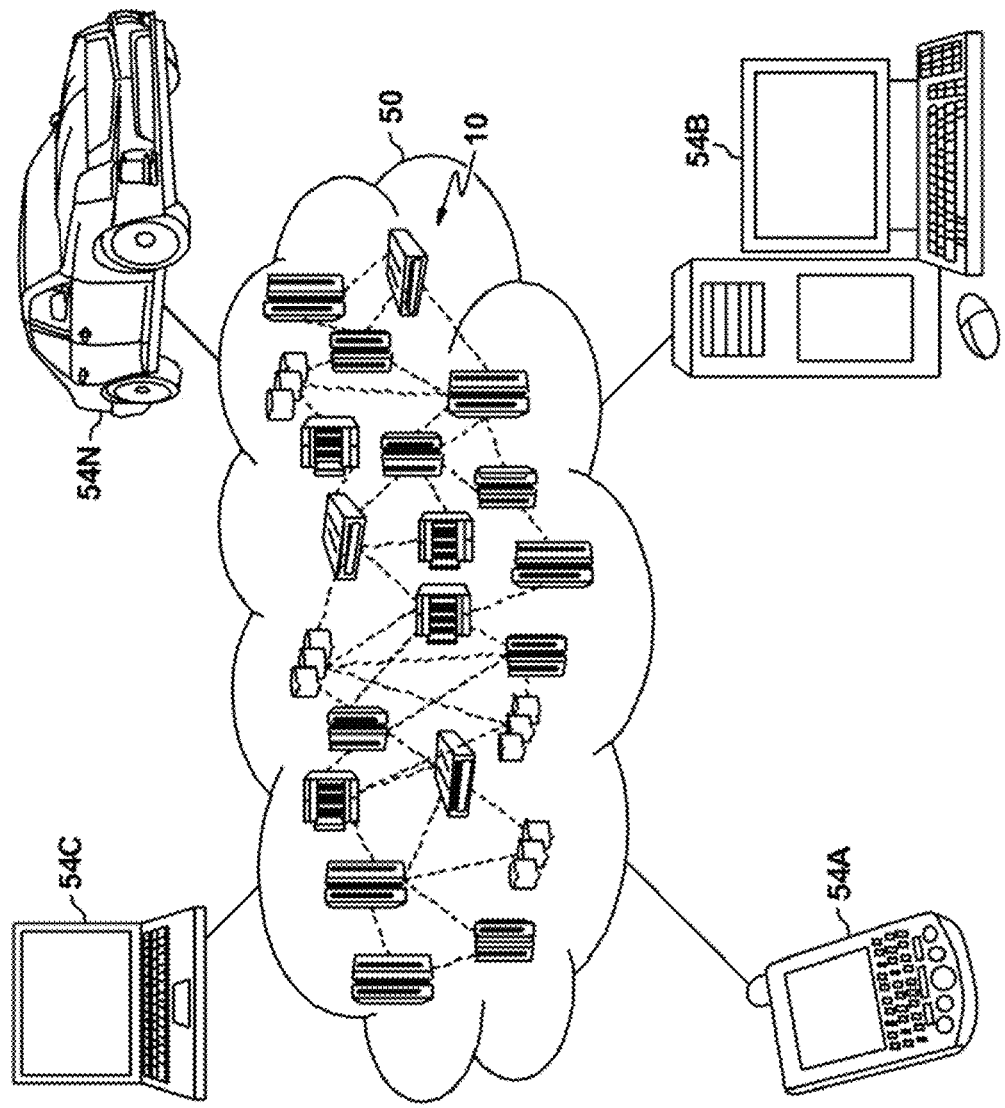
FIG. 6 is a functional block diagram 50 of a collection of computing devices or cloud computing nodes, such as the one depicted in FIG. 5, according to an embodiment of the invention.
Figure 7:
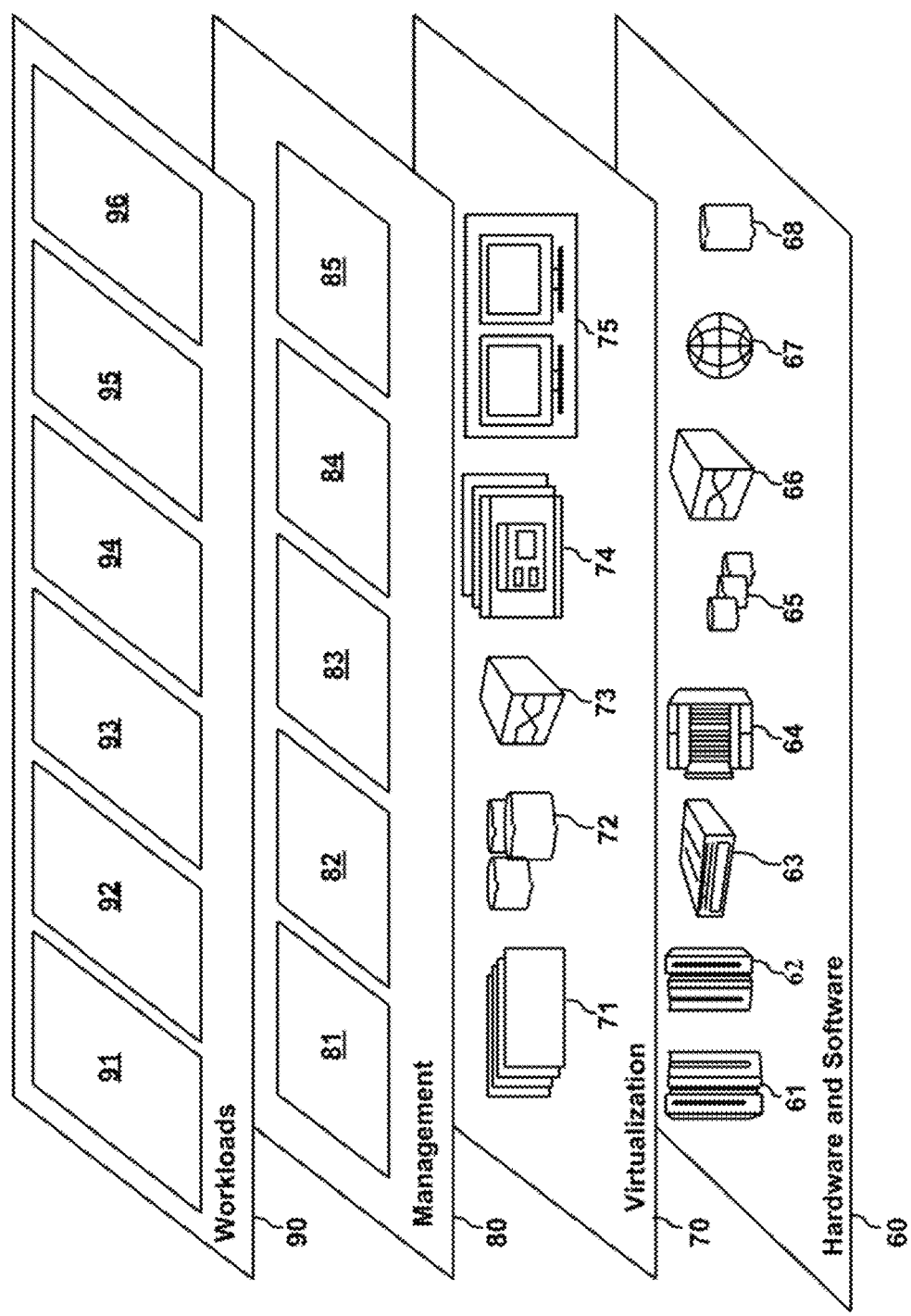
FIG. 7 is a functional block diagram of functional layers of the cloud computing environment of FIG. 6, according to an embodiment of the invention.

As described above in connection with the Background of embodiments of the invention, a healthcare system may be configured as a cloud computing platform for healthcare. An exemplary embodiment of the configuration and functional operation of such a cloud computing platform is depicted in FIGS. 5, 6, and 7.

According to an embodiment of the invention, the cloud computing platform for healthcare is a multi-tenant healthcare platform that stores and processes Electronic Health Records (EHRs), Protected Healthcare Information (PHI), and Medical Event data (collectively, "healthcare data"). The cloud computing platform for healthcare may be accessible by, and the healthcare data may belong to, multiple users, including healthcare provides, facilities, vendors, customers, patients, and other organizations and individuals. In one embodiment, data is added to the cloud computing platform for healthcare using an Extraction-Transformation-Load (ETL) pipeline. Using this pipeline, data is loaded into a data lake, data reservoir, and data mart. As a new data element arrives for loading, a pipeline executes stages that collectively perform an ETL operation to load the data into the cloud computing platform for healthcare. The new data element may be, for example, a "Health Level 7" (HL7) message, an "Admission Discharge, Transfer" (ADT) message, or a "Fast Healthcare Interoperability Resource" (FHIR) bundle.

The ETL data may arrive as a stream of one or more message. Whether these messages are 1 Kilobyte, 100 Kilobytes, or 10 Megabytes in size, their processing requires many seconds to fully process through the ETL logic. This is particularly the case because the medical data, i.e., data elements in the incoming data stream, have a high degree of outbound references; for example, "Medication", "Medication Orders", "Medical Devices", "Observations" and "Medical Events" data. As new messages are queued for processing, the ETL logic is forced to sequentially process the loading of the data processing system. As an intermediate step, the ETL logic spreads the load out across many worker threads, which execute the ETL logic. This ETL logic only scales so far for highly referential data elements as the data elements are loaded into the data processing systems. For example, as the frequency of incoming data increases, it can indiscriminately trigger ETL logic that consumes too much computing resources and makes the platform for healthcare inefficient.

Providing real-time access to healthcare insights using the ETL model requires optimization of access to the underlying data while minimizing downstream churn (for example, the need to continually reprocess and re-evaluate data). Embodiments of the invention provide a beneficial balance between the need for real-time access to data and avoidance of inefficient data processing.

Embodiments of the invention may be used for more than one application or tenant. As such, a tenant configuration may include: a set of insight queries for specific adherence and administration calculations and a set of specific dimensional models and data schemas. Embodiments of the invention may be used for more than one application and multiple tenants. Embodiments of the invention may be referential, normalized or de-normalized. Embodiments of the invention may apply to fixed or server-less infrastructure. Embodiments of the invention apply to any time of data processing—Near-Realtime (NRT), Batch, or Bulk.

Some embodiments of the invention will now be described in more detail in connection with the Figures.

Figure 1:
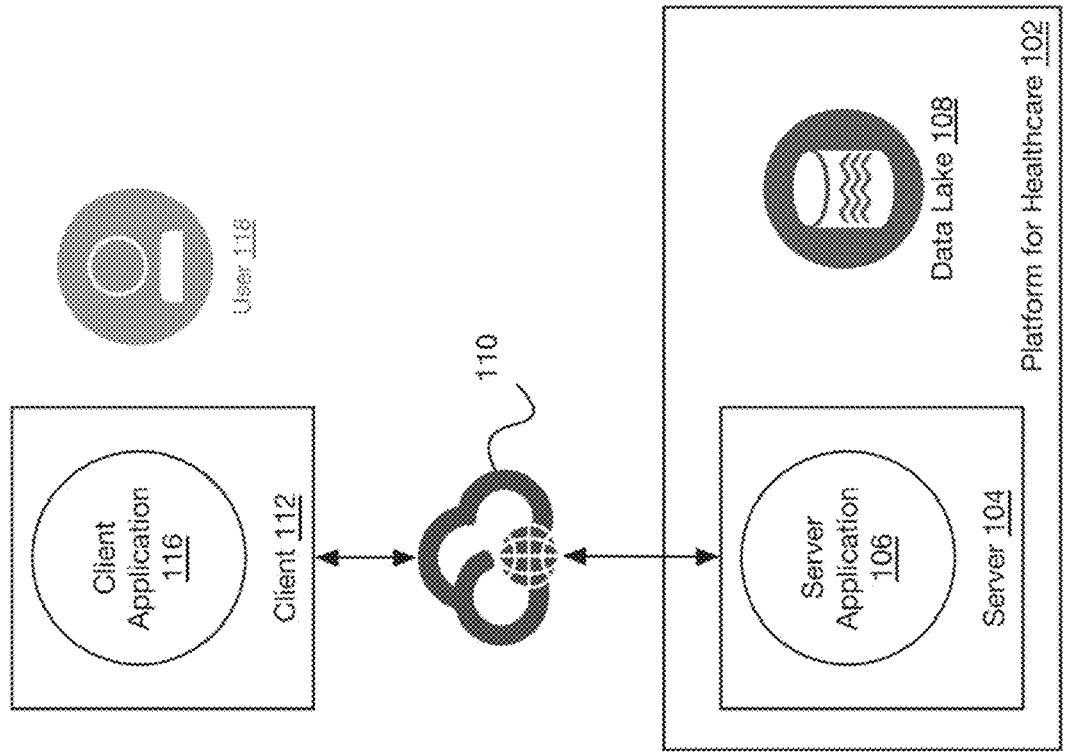
FIG. 1 is a functional block diagram of an illustrative distributed computing environment 100, according to an embodiment of the invention.

FIG. 1 is a functional block diagram of an illustrative distributed computing environment 100, according to an embodiment of the invention.

Referring now to FIG. 1, distributed computing environment 100 includes cloud computing platform for healthcare 102 ("platform for healthcare 102"). Platform for healthcare 102 includes one or more operatively connected computing devices as described in connection with FIGS. 5-7 that collectively provide computing services and perform computing functions in healthcare use cases. These computing devices of platform for healthcare 102 include a server 104 and a data lake 108.

Server 104 includes a computing device having one or more processors and one or more tangible storage media for storing programming instructions of one or more computer applications, including a server application 106. Server application 106 receives input data, process the input data, and generates output data, to enable one or more functions of platform for healthcare 102. Server 104 is operatively connected to a network 110 through which it connects to one or more other devices outside of platform for healthcare 102.

Data lake 108, in its most general sense, refers to a data repository. In the context of platform for healthcare 102, it refers to a single point of storage for at least some collections of data that platform for healthcare 102 processes and manages. For example, in one implementation, all patient raw data (such as EHRs) may be stored in data lake 108. The stored data may be in its natural or raw format. Data lake 108 can include structured data from relational databases (rows and columns), semi-structured data (CSV, logs, XML, JSON), unstructured data (emails, documents, PDFs) and binary data (images, audio, video). Other groupings of data are also possible (such as a data reservoir, and data mart). Such groupings of data can be configured in various embodiments of the invention to facilitate the objectives of the particular implementation of distributed computing environment 100, and may be based on the nature and size of the data to be managed and processed, or by the number or type of users and other actors interacting with distributed computing environment 100.

In the embodiment depicted in FIG. 1, a Data Lake 108 stores healthcare data for management and processing. Data Lake 108 may have one or more databases, such as one or more shared physical HBase tables; HBase is an open-source non-relational distributed database. The Shared physical HBase may include an HBase Table constituting an "FHIR Data Lake" (storing FHIR data) and an HBase Table constituting a "Raw Data Lake" (storing raw data).

Network 110 can be, for example, a local area network (LAN), a wide area network (WAN) such as the Internet, or a combination of the two, and can include wired, wireless, or fiber optic connections. In general, network 110 can be any combination of connections and protocols that will support communications between two computing devices.

Client 112 device can be a laptop computer, tablet computer, netbook computer, personal computer (PC), a desktop computer, a personal digital assistant (PDA), a smart phone, a smart watch, or any programmable electronic device capable of communicating with server 104 via network 110. Client 112 device includes client application 116, having a set of programming instructions that can execute locally or remotely.

One or more users 118 can operate or interact with the various devices of distributed computing environment 100.

Figure 2:
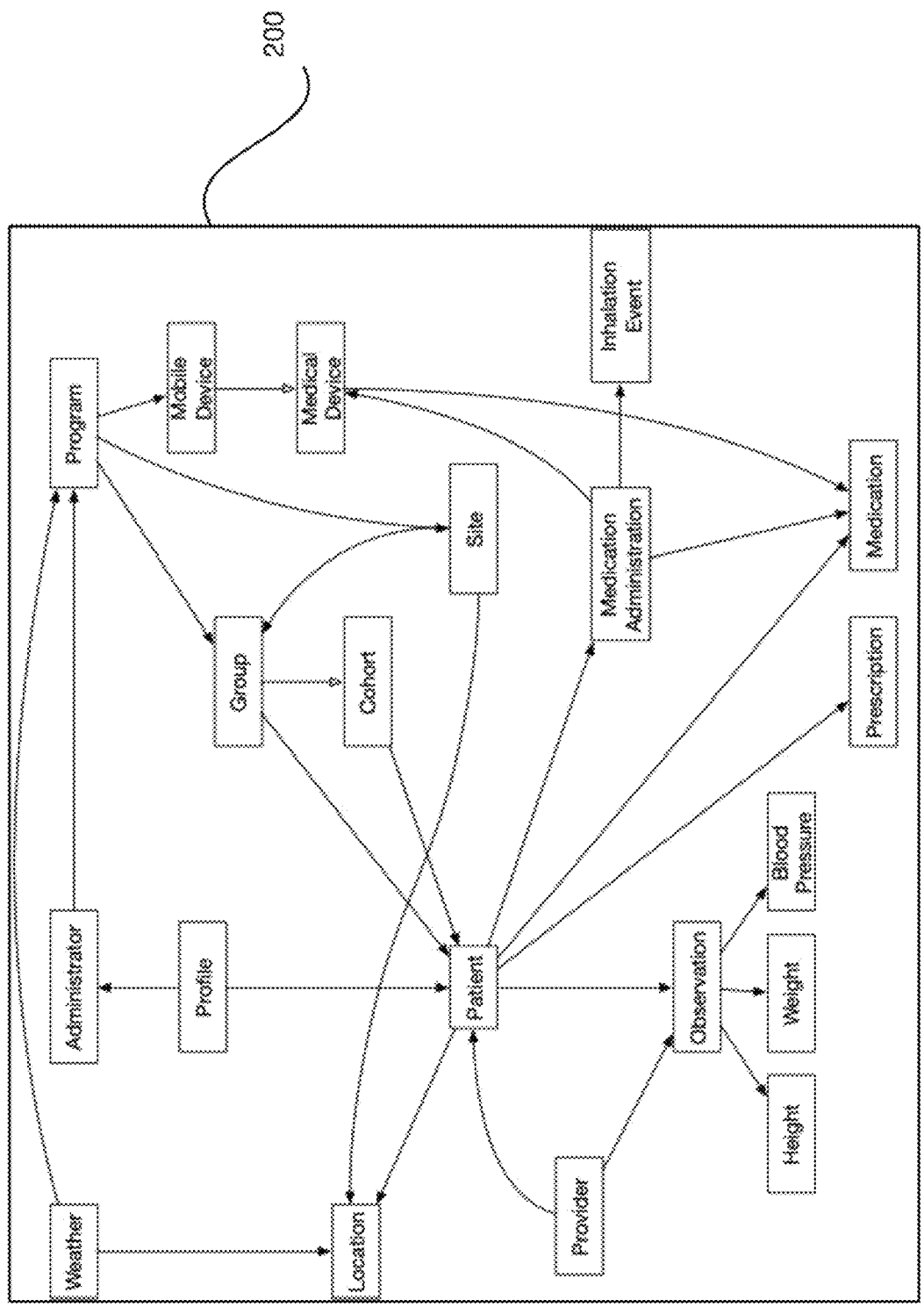
FIG. 2 is a block diagram of an entity relationship model 200 used in distributed computing environment 100 of FIG. 1, according to an embodiment of the invention.

FIG. 2 is a block diagram of an entity relationship model 200 ("model 200") used in distributed computing environment 100 of FIG. 1, according to an embodiment of the invention.

Referring now to FIGS. 1 and 2, consider the following illustrative scenario: User 118 suffers from or is at risk of developing diabetes. User 118 is prescribed a diabetes protocol by his physician to treat or prevent diabetes. User 118 installs client application 116 on client device 112 to aid her in the process. In this scenario, client application 116 is a healthcare application, and client device 112 is a smartphone. The smartphone continuously monitors the user's glucose levels (for example, via readings by a glucose reader). The healthcare application on the smartphone syncs its data, including updated glucose monitoring data, with server application 106 via network 110. The synced information may exclude FHIR data and demographic data to preserve patient privacy as a matter of preference or to comply with applicable data privacy policies or laws. In this scenario, server application 106 drivers push the synced data into data lake 108 using an FHIR resource bundle. Platform for healthcare 102 processes the FHIR resource bundle (including, for example, patient data, observation data, patient ID, and other information).

The manner in which platform for healthcare 102 performs this data processing can impact its performance. If the processing is infrequent, then data analysis functions performed or enabled by platform for healthcare 102 may be unreliable or outdated; because they will have been performed without processing certain data relevant to the outcomes of those functions. On the other hand, if the processing is too frequent, the entire system may be bogged down; it cannot provide useful functions because it is always busy updating information based on continuous data updates.

It is therefore desirable for platform for healthcare 102 to process the FHIR resource bundle (or other data) to achieve one or more processing objectives, as described in connection with embodiments of the invention.

With continued reference to FIGS. 1 and 2, and to the illustrative scenario described above, model 200 includes a set of entities and their relationships. The entities and their relationships (denoted by connections) generally provide information that identifies a patient, patient demographics, medical history, observational data, device data, insurance data, events data, and other information. The information generally allows a healthcare application (such as client application 116), or a healthcare system (such as platform for healthcare 102) to provide healthcare-related computing functions.

In the case of the illustrative scenario, the data in model 200 can include patient data (e.g., identification information) and observation data, such as continuous glucose monitoring (CGM) data collected or tracked via client 112 device and client application 116. More specifically, in the depicted embodiment, the data in model 200 comprises a patient having a profile accessible by an administrator that provides or operates a computer program. The computer program is installable on a mobile device of the patient and communicates (e.g., wirelessly via Bluetooth® or WiFi) with one or more medical devices (e.g., blood glucose reader). The medical device may monitor medications and medication administration by the patient. Medication administration may be associated with an inhalation event. The program may monitor a group of patients to which the patient belongs, and may determine or monitor a set of cohorts. The group may be associated with a site (e.g., a hospital or other medical practice) or an area in which the patient resides; the site(s) may have an associated location and weather information that the program tracks. The patient also may have an associated provider, such as a medical provider. The patient may receive, via visits to the provider, observation data, such as height, weight, and blood pressure. The patient may receive prescriptions for medications, for example as a result of visits to the medical provider.

Model 200 may be stored in a datastore (for example, in data lake 108). One instance of the data may include, for example, the following data:

Observation[CGM] Cardinality: Patient→Observation=1000

Data Size=1M entries per Patient

Schema=Dimension and Array update in Star Schema

In the case of the illustrative scenario above, platform for healthcare 102 may determine, for example, that the cardinality for observation in this case is low. Platform for healthcare 102 may therefore delay loading of this data for use in data compilation, as its impact is low, and any insertion may cause an immediate and costly recompilation across a wide set of data. Delaying loading of the data ensures that its processing is performed along with a sufficient number of additional data that maintain system-wide efficiency.

Figure 3:
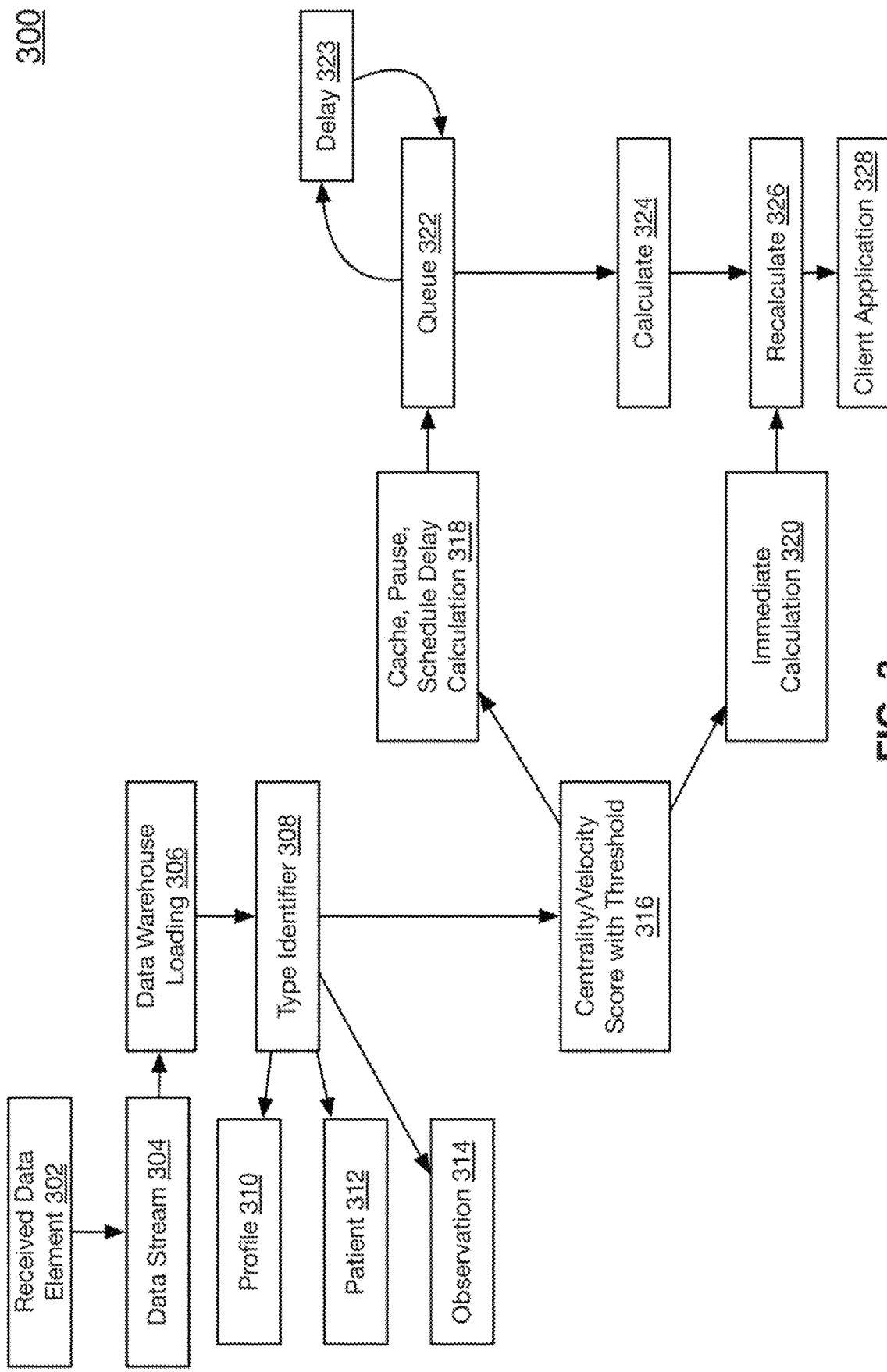
FIG. 3 is a flowchart of a method 300 for dynamically moderating healthcare application data, according to an embodiment of the invention.

FIG. 3 is a block diagram of functional stages 300 of server application 106 for dynamically moderating healthcare application data, according to an embodiment of the invention. Functions of method 300 are performed via one or more processors executing programming instructions stored on one or more tangible storage media. Programming instructions of functional stages 300 may be part of one or more applications, such as server application 106 and client application 116 of FIG. 1 and may use data elements of model 200.

Referring now to FIGS. 1-3, platform for healthcare 102 receives via server application 106 one or more data elements 302 (each of which may be a data element 200 of FIG. 2) from client application 116, as part of a data stream 304. Platform for healthcare 102 loads the data element into data lake 108 as part of a data warehouse loading stage 306, and then processes via a custom set of ETLs to load into an analytical warehouse. In an embodiment, the ETL is based on DataStage® and Java®.

Processing the data element may include processing by a type identifier 308 component to identify profile data 310, patient data 312, and observation data 314 (such as its date). Processed data may then move to a centrality/velocity scorer 316 that classifies, using a threshold value, whether to immediately calculate values at an immediate calculation stage 320 for insight compilation and presentation, or to instead to process the data stage 318 for cache, pause, or delay calculation.

The calculation stage of stage 318 involves a queuing stage 322 that queues calculation operations. A delaying mechanism 323 allows for controlled execution according to a schedule. Queued data elements are calculated at stage 324 according to a calculation schedule. A new data element triggers a recalculation when it is ready for processing, at stage 326. Resulting insights are then compiled and presented to the client application 116 at stage 328.

Figure 4:
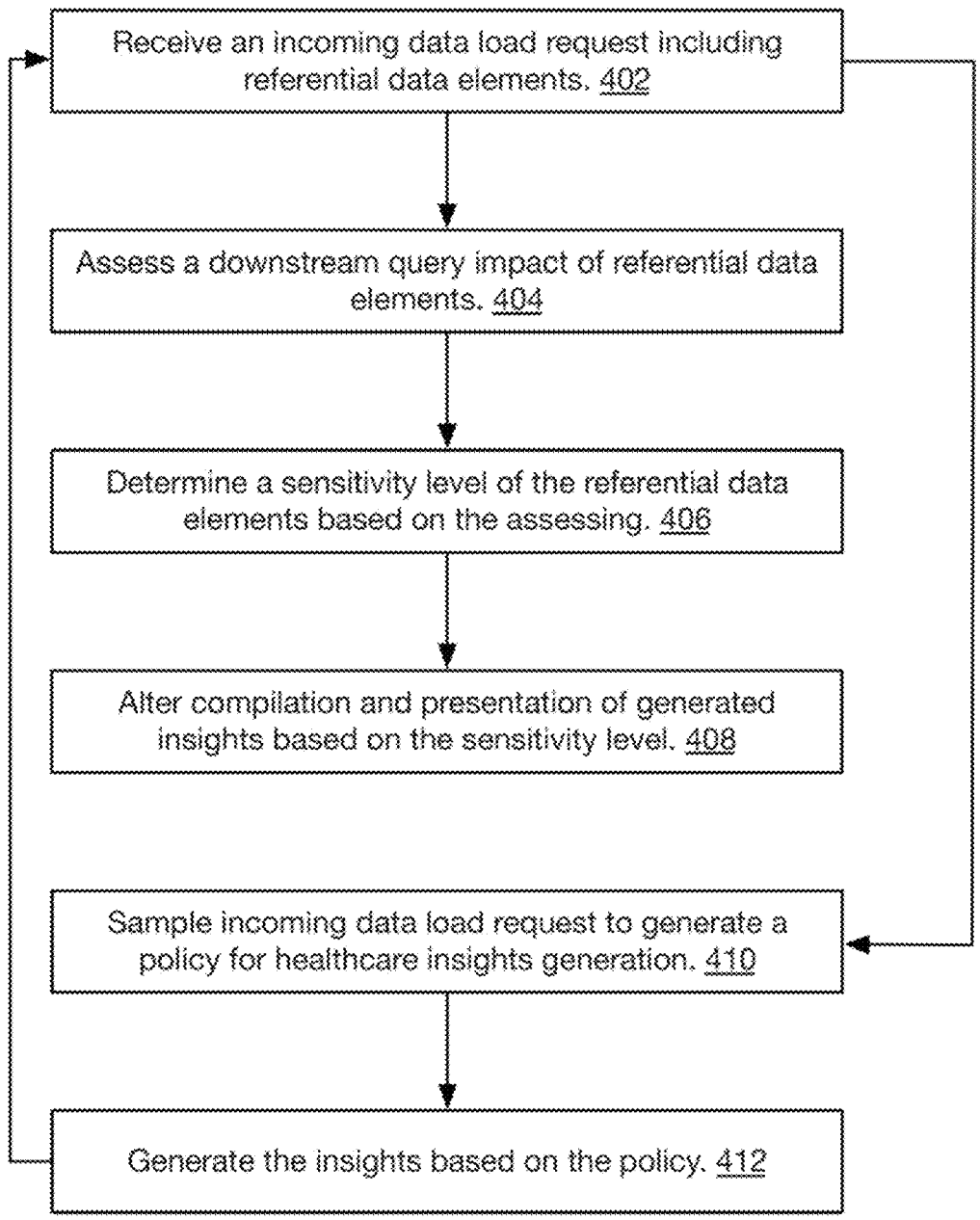
FIG. 4 is a flowchart of a method 400 for dynamically moderating healthcare application data, according to an embodiment of the invention.

FIG. 4 is a flowchart of a method 400 for moderating healthcare application data, according to an embodiment of the invention. Steps of method 400 are performed by executing one or more programming instructions by one or more processors of one more computer system. The programming instructions may be stored on one or more computer program products including tangible storage media. For example, steps of method 400 may be performed by server application 106 of platform for healthcare 102, by client application 116 of client 112 device, or by a combination thereof, as shown in FIG. 1. For simplicity, functions of method 400 will be described below as performable by sever application 106.

Referring now to FIGS. 1 and 4, server application 106 receives (step 402) an incoming data load request including referential data elements. As part of this step, server application receives an incoming data load, which is associated with a healthcare application (for example, client application 116), a set of queries, and a schema as part of a bundle. For each resource in the bundle, server application 106 determines the resource type and the field references in the data. If this is the first time method 400 is performed, or if its operations are reset, then server application 106 samples (step 410) the incoming data in order to build a policy for the healthcare insights based on the healthcare data, such that a more generic policy can be generated for data usage priority, decision support sensitivity (daily, statistical), network bandwidth (downloaded, cached, capacity), and maximal batch size (e.g., 10,000 downloaded, recalculate), and applied with minimal CPU/Memory usage. Insights are generated (step 412) based on the policy. Method 400 is performed again upon receiving (step 402) additional incoming data load requests.

Server application 106 assesses (step 404) a downstream query impact of referential data elements in the received data load request (step 402). Assessing the downstream query impact is performed using the object-role-modelling (ORM) approach, or an ontology definition (for example, FHIR DSTU2), to place the resource type into a model graph and determine if it is a central node or an outer node. More specifically, server application 106 determines the placement of the data in the parse tree (for example, entity relationship model 200) and the query plan for the downstream application queries. This can be performed, in an embodiment, using code shown in Table 1, below.

TABLE 1 determining placement of data in parse tree

StmtText
----
 |--Sort (ORDER BY: ( [c] . [LastName] ASC) )
     |--Nested Loops (Inner Join, OUTER
REFERENCES: ( [e] . [ContactID], [Expr1004] ) WITH UNORDERED PREFETCH)
     |--Clustered Index
Scan (OBJECT: ( [AdventureWorks] . [HumanResources] . [Employee] . [PK_Employee_
EmployeeID] AS [e] ) )

TABLE 1-continued determining placement of data in parse tree

|--Clustered Index
Seek (OBJECT: ( [AdventureWorks] . [Person] . [Contact] . [PK_Contact_ContactID]
AS [c] ) ,
SEEK: ( [c] . [ContactID] = [AdventureWorks] . [HumanResources] . [Employee] .
[ContactID] as [e] . [ContactID] ) ORDERED FORWARD)

The data is placed and associated with the cardinality related to the query. Server application 106 further analyzes counts in the table per each patient ID, and determines the split/delivery counts per patient per table on average, and uses the data to indicate sensitivity in another step.

With continued reference to FIGS. 1 and 4, server application 106 determines (step 406) a sensitivity level of the referential data elements, based on the assessment (step 404). Server application 106 determines (step 406) a total sensitivity by aggregating changes to the cardinality of the data set (inner or outer join), the number of tables touched in the query—Snow Flake (inner branch, outer leaf, and the frequency of the data. Based on the aggregation, server application 106 assigns the data to a bucket as sensitive or insensitive to the change.

Server application 106 alters (step 408) compilation and presentation of generated insights based on the sensitivity level that is determined (step 406). The function of altering (step 408) is performed by delaying the compilation of data, locking the related resources, or incrementally updating the tables to spread the compilation recalculation costs or big-bangs the compilation to get the cost absorbed. Data presentation by server application 106 includes functions of cache, content-no-yet-updated, read stability, lock until updated, immediate data load, delayed load until set time, and moderate recompilation for a given patient.

Server application 106 can thus moderate the delivery quality of the presentation by modifying a variety of properties—bandwidth, compressibility, information gain, entropy, batch size, sensitivity and usage priority.

Server application 106 may use the statistics to recalculate and change the sample rate of the data loading in order to get a more precise execution pattern for the compilation sensitivity.

FIG. 5 is a block diagram of an illustrative cloud computing node, according to an embodiment of the invention. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove (for example, in connection with FIGS. 1-4, above, and particularly first storage device 706, IoT devices, and other components described in connection with FIG. 7).

In cloud computing node 10 there is a computer system/server 12, which is operational with numerous other general purposes or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

FIG. 6 is a block diagram of a cloud computing environment including the cloud computing node of FIG. 5, according to an embodiment of the invention. Referring now to FIG. 4, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that cloud computing nodes 10 and cloud computing environment 50 can communicate with any type of computerized device over any type of network and/or network addressable connection (e.g., using a web browser).

FIG. 7 is a block diagram of functional layers of the cloud computing environment of FIG. 4, according to an embodiment of the invention. Referring now to FIG. 6, a set of functional abstraction layers provided by cloud computing environment 50 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; moderating healthcare application data 96, including those described in connection with FIGS. 1-4, above.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer implemented method for dynamically moderating real-time healthcare application data in a multitenant healthcare platform storing and processing electronic healthcare records in a cloud environment while minimizing downstream churn, minimizing churn including minimizing the need to process and re-process data, the method comprising:

receiving by a server application associated with the multitenant healthcare platform an incoming real-time data load request comprising a plurality of referential healthcare data elements related to healthcare data regarding a patient, the data load request related to loading healthcare data into the server application;

assessing a downstream query impact of the plurality of referential data elements, the impact related to performance of the multitenant healthcare platform;

determining, based on the assessing, a sensitivity level of the plurality of referential data elements, the sensitivity level related to a cardinality of the referential healthcare data elements and a number of changes to be made to a data set;

classifying, at a centrality/velocity scorer, the referential data, wherein classifying uses a threshold value to immediately calculate values at an immediate calculation stage or to process the referential data at a queuing stage;

delaying loading, at the queuing stage, the referential data elements into the server application based on the cardinality below a threshold, wherein a delaying mechanism allows for controlled execution to a schedule; and altering, based on the sensitivity level, compilation of insights based on healthcare data compilation generated using the plurality of referential data elements and compilation of a plurality of referenced data elements.

2. The method of claim 1, further comprising:
altering, based on the sensitivity level, presentation of the insights.

3. The method of claim 2, wherein presentation of the insights comprises:
a caching function;
a content-not-yet-updated function;
a read stability function;
a lock-until-updated function;
an immediate data load function;
a delayed load-until-set-time function; or
a moderate recompilation function.

4. The method of claim 1, further comprising:
sampling the incoming data load request, including the plurality of referential data elements, to generate a policy for healthcare insights generation.

5. The method of claim 4, further comprising:
generating the insights based on the policy.

6. The method of claim 1, wherein determining the sensitivity level comprises aggregating:
changes to cardinality of the incoming data load request;
a number of tables touched in the query; and
a frequency of the data.

7. The method of claim 1, wherein the altering comprises:
locking related resources; or
incrementally updating tables to spread compilation recalculation costs.

8. The method of claim 1, wherein the incoming data requests comprise a single request, multiple requests, or one or more bundled requests.

9. A computer program product for dynamically moderating real-time healthcare application data in a multitenant healthcare platform storing and processing electronic healthcare records in a cloud environment while minimizing downstream churn, minimizing churn including minimizing the need to process and re-process data, the computer program product comprising one or more computer readable storage media, and program instructions collectively stored on the one or more computer readable storage media for execution by one or more processors to perform a method, the program instructions comprising instructions for:
receiving, by the one or more processors executing a server application associated with the multitenant healthcare platform, an incoming real-time data load request comprising a plurality of referential healthcare data elements related to healthcare data regarding a patient, the data load request related to loading healthcare data into the server application;
assessing, by the one or more processors, a downstream query impact of the plurality of referential data elements, the impact related to performance of the multitenant healthcare platform;
determining, by the one or more processors, based on the assessing, a sensitivity level of the plurality of referential data elements, the sensitivity level related to a cardinality of the referential healthcare data elements and a number of changes to be made to a data set;
classifying, at a central/velocity scorer, the referential data, wherein classifying uses a threshold value to immediately calculate values at an immediate calculation stage or to process referential data at a queuing stage;
delaying loading, at the queuing stage, the referential data elements into the server application based on the cardinality below a threshold, wherein a delaying mechanism allows for controlled execution to a schedule; and
altering, by the one or more processors, based on the sensitivity level, compilation of insights based on healthcare data compilation generated using the plurality of referential data elements and compilation of a plurality of referenced data elements.

10. The computer program product of claim 9, the instructions further comprising:
altering, by the one or more processors, based on the sensitivity level, presentation of the insights.

11. The compute program product of claim 10, wherein presentation of the insights comprises:
a caching function;
a content-not-yet-updated function;
a read stability function;
a lock-until-updated function;
an immediate data load function;
a delayed load-until-set-time function; or
a moderate recompilation function.

12. The computer program product of claim 9, the instructions further comprising:
sampling, by the one or more processors, the incoming data load request, including the plurality of referential data elements, to generate a policy for healthcare insights generation.

13. The computer program product of claim 12, the instructions further comprising:
generating, by the one or more processors, the insights based on the policy.

14. The computer program product of claim 9, wherein determining the sensitivity level comprises aggregating, by the one or more processors:
changes to cardinality of the incoming data load request;
a number of tables touched in the query; and
a frequency of the data.

15. The computer program product of claim 9, wherein the altering comprises:
locking, by the one or more processors, related resources; or
incrementally updating, by the one or more processors, tables to spread compilation recalculation costs.

16. The computer program product of claim 9, wherein the incoming data requests comprise a single request, multiple requests, or one or more bundled requests.

17. A computer system for dynamically moderating real-time healthcare application data managing data in a multitenant healthcare platform storing and processing electronic healthcare records in a distributed computing environment while minimizing downstream churn, minimizing churn including minimizing the need to process and re-process data, the computer system comprising:
one or more processors and one or more programming instructions stored on one or more tangible storage media of the computer system, the programming instructions being executable by the one or more processors to perform a method, the programming instructions comprising instructions for:
receiving by a server application associated with the multitenant healthcare platform an incoming real-time data load request comprising a plurality of referential healthcare data elements related to healthcare data regarding a patient, the data load request related to loading healthcare data into the server application;

assessing a downstream query impact of the plurality of referential data elements, the impact related to performance of the multitenant healthcare platform;

determining, based on the assessing, a sensitivity level of the plurality of referential data elements, the sensitivity level related to cardinality of the referential healthcare data elements and a number of changes to be made to a data set;

classifying, at a centrality/velocity scorer, the referential data, wherein classifying uses a threshold value to immediately calculate values at an immediate calculation stage or to process the referential data at a queuing stage;

delaying loading, at the queuing stage, the referential data elements into the server application based on the cardinality below a threshold, wherein a delaying mechanism allows for controlled execution to a schedule; and altering, based on the sensitivity level, compilation of insights based on healthcare data compilation generated using the plurality of referential data elements and compilation of a plurality of referenced data elements.

18. The computer system of claim 17, the instructions further comprising:

altering, based on the sensitivity level, presentation of the insights.

* * * * *